(12) United States Patent
Chua et al.

(10) Patent No.: US 7,451,762 B2
(45) Date of Patent: Nov. 18, 2008

(54) PRESSURE SENSING DEVICE WITH TEST CIRCUIT

(75) Inventors: James Chua, Bakersfield, CA (US);
Kyle Adriance, Bakersfield, CA (US);
Phuoc H. Vo, El Monte, CA (US)

(73) Assignee: Salter Labs, Arvin, CA (US)

( * ) Notice: Subject to any disclaimer, the term of this patent is extended or adjusted under 35 U.S.C. 154(b) by 524 days.

(21) Appl. No.: 11/155,902

(22) Filed: Jun. 17, 2005

(65) Prior Publication Data
US 2006/0283446 A1    Dec. 21, 2006

(51) Int. Cl.
*A61M 16/00* (2006.01)
(52) U.S. Cl. .................................. 128/204.23
(58) Field of Classification Search ............ 128/204.18, 128/204.21, 204.22, 204.23
See application file for complete search history.

(56) References Cited

U.S. PATENT DOCUMENTS

| | | | |
|---|---|---|---|
| 6,668,828 B1 * | 12/2003 | Figley et al. ............ | 128/204.18 |
| 6,849,049 B2 * | 2/2005 | Starr et al. ................... | 600/538 |
| 7,246,619 B2 * | 7/2007 | Truschel et al. ......... | 128/204.26 |
| 2006/0169281 A1 * | 8/2006 | Aylsworth et al. ..... | 128/204.23 |
| 2007/0113850 A1 * | 5/2007 | Acker et al. ............ | 128/204.22 |
| 2007/0277824 A1 * | 12/2007 | Aylsworth et al. ..... | 128/204.23 |

OTHER PUBLICATIONS

Dr. David Rapoport, M.D., Robert Norman, M.S., R.R.T., Michael Nielson, R.R.T., R.PSG.T., "Nasal Pressure Airflow Measurement", Copyright 2001 by Pro-Tech Services, Inc. (43 pgs).

* cited by examiner

*Primary Examiner*—Steven O Douglas
(74) *Attorney, Agent, or Firm*—Davis Bujold & Daniels, P.L.L.C.

(57) ABSTRACT

A pressure sensing device for coupling to a cannula and receiving respiratory breathing information from a patient to be monitored. The pressure sensing device comprising an exterior housing accommodating a snore detection circuit which processes information and outputs a signal indicative; an airflow detection circuit which processes information and outputs a signal indicative thereof; and an internal test circuit for testing an integrity of the airflow and snore detection circuits prior to use of the pressure sensing device to ensure that both circuits are operational. An input port for pressure sensing device extends from the housing of the pressure sensing device so as to space a connector, for the cannula, a sufficient distance away from the bottom surface whereby the bottom surface will always remain flush with and in constant and continuous intimate contact with a support surface for the pressure sensing device.

20 Claims, 13 Drawing Sheets

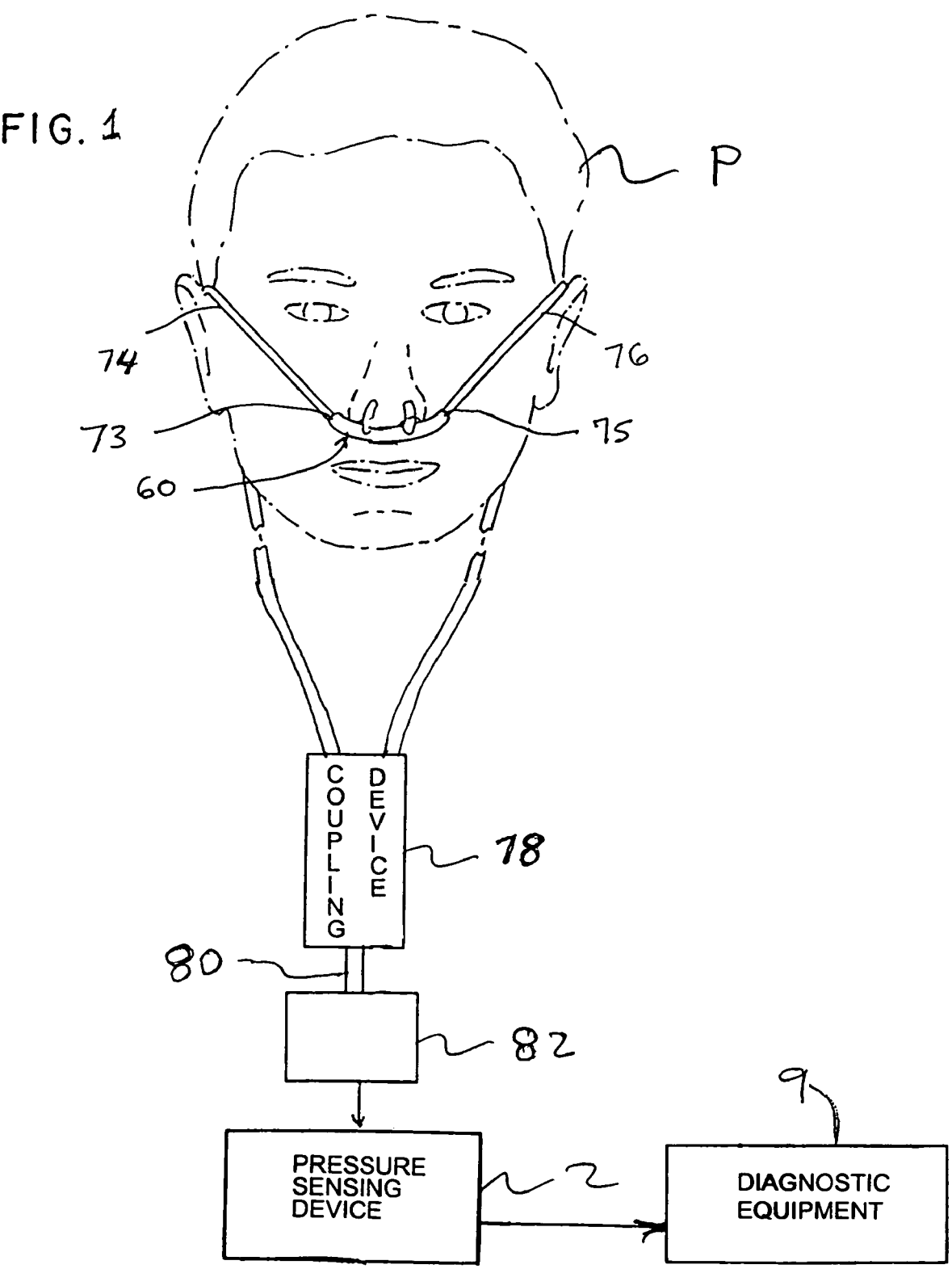

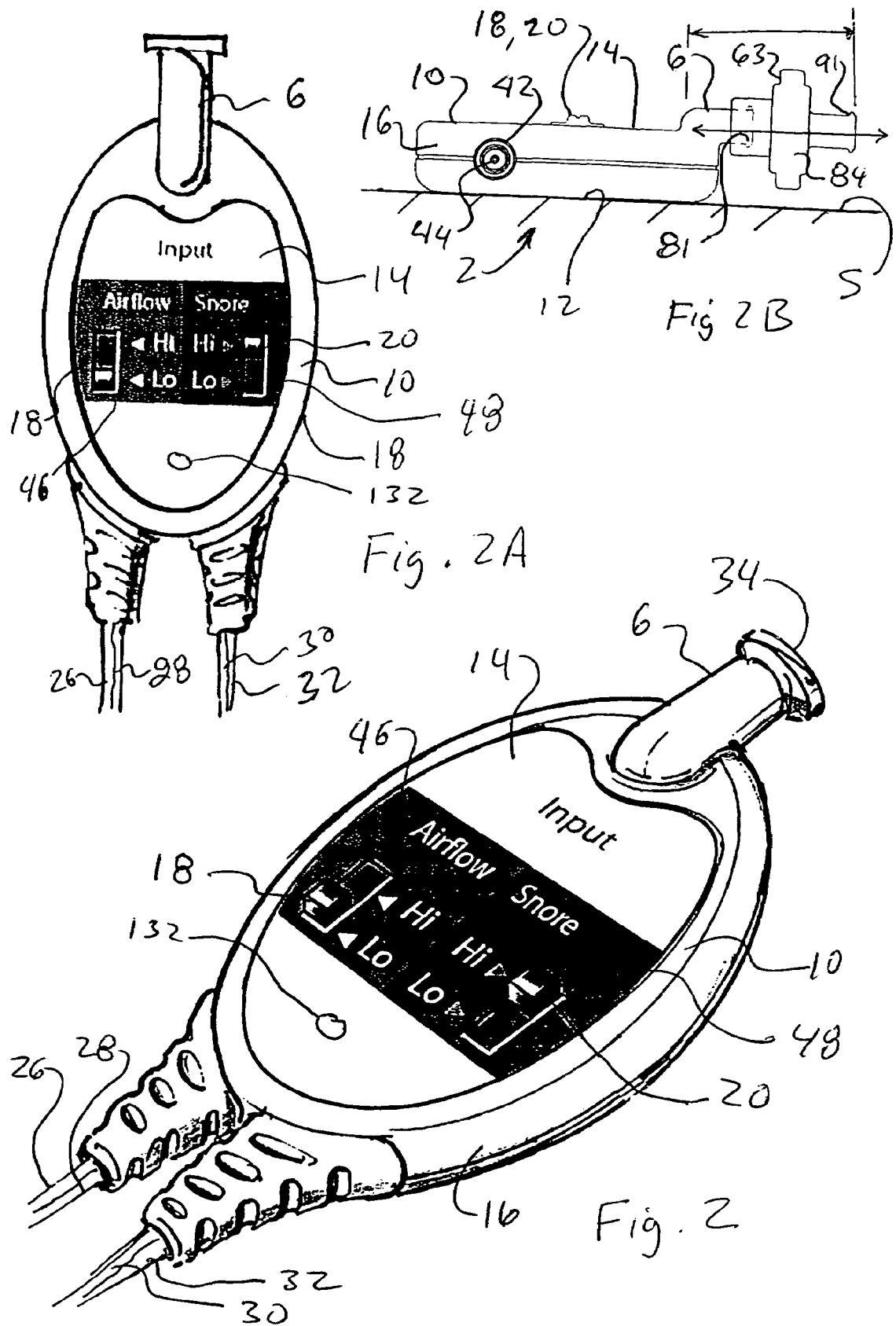

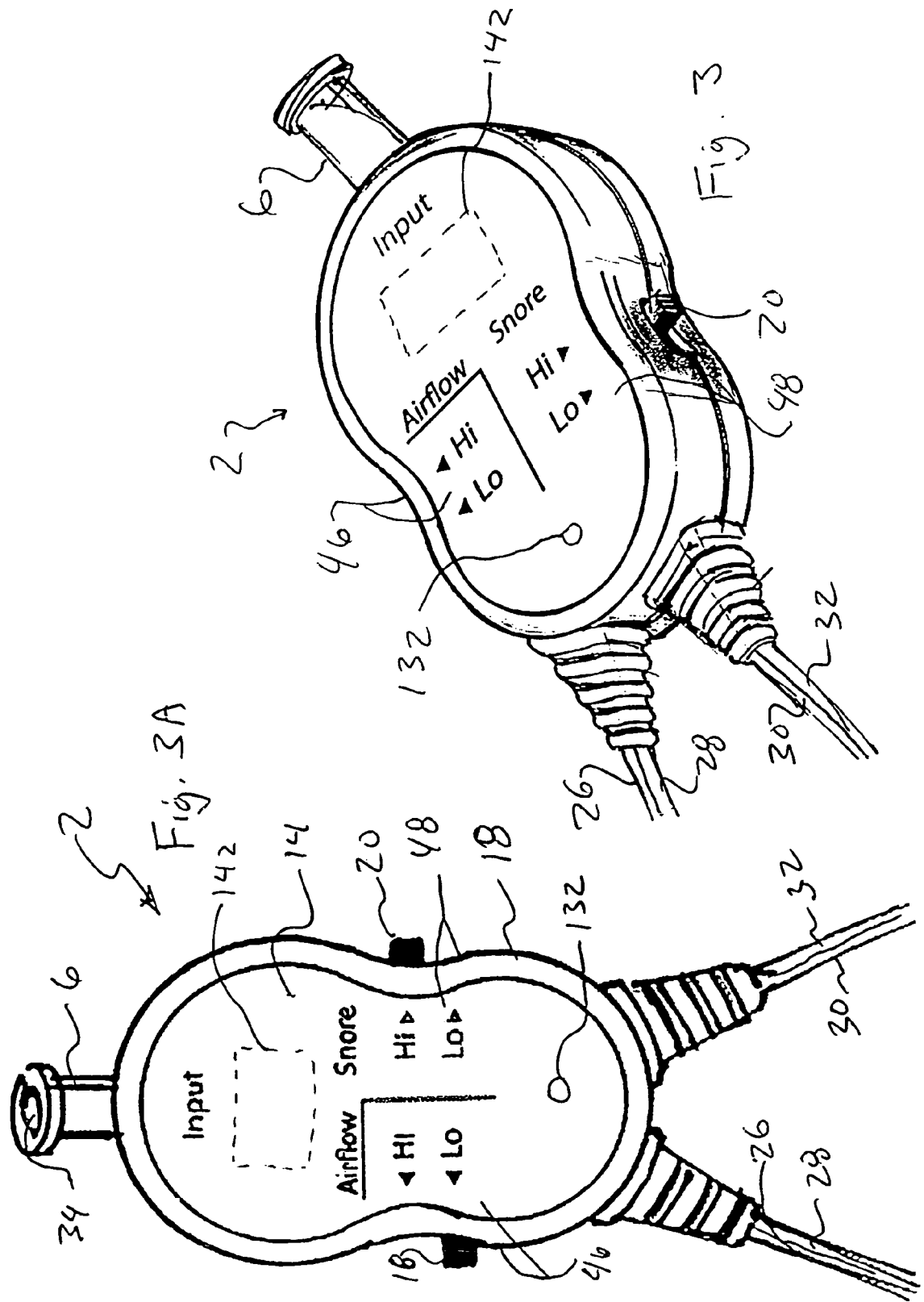

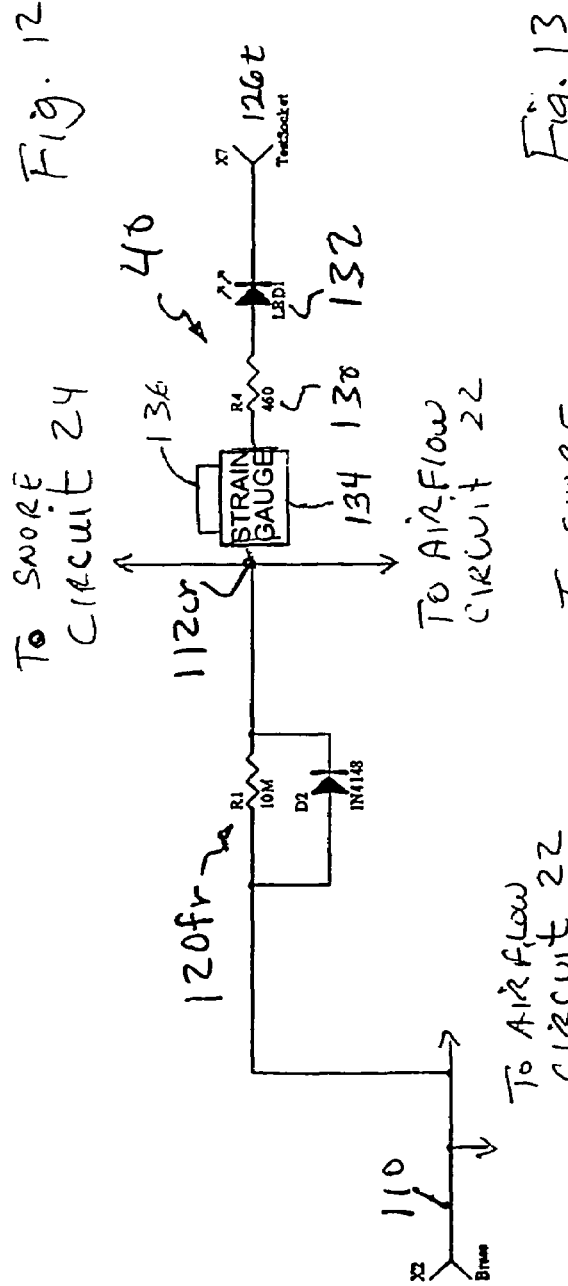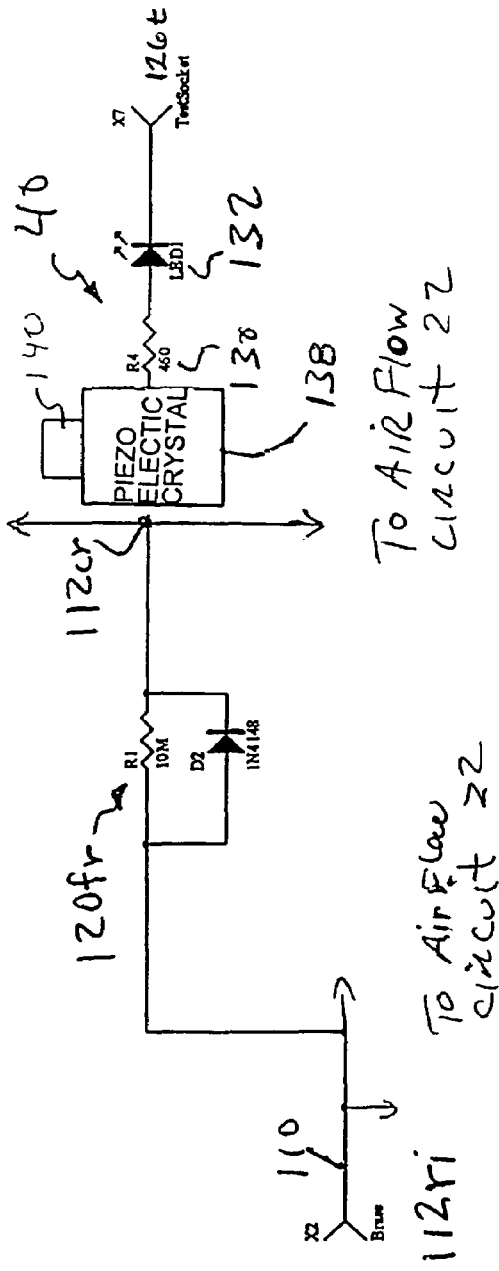

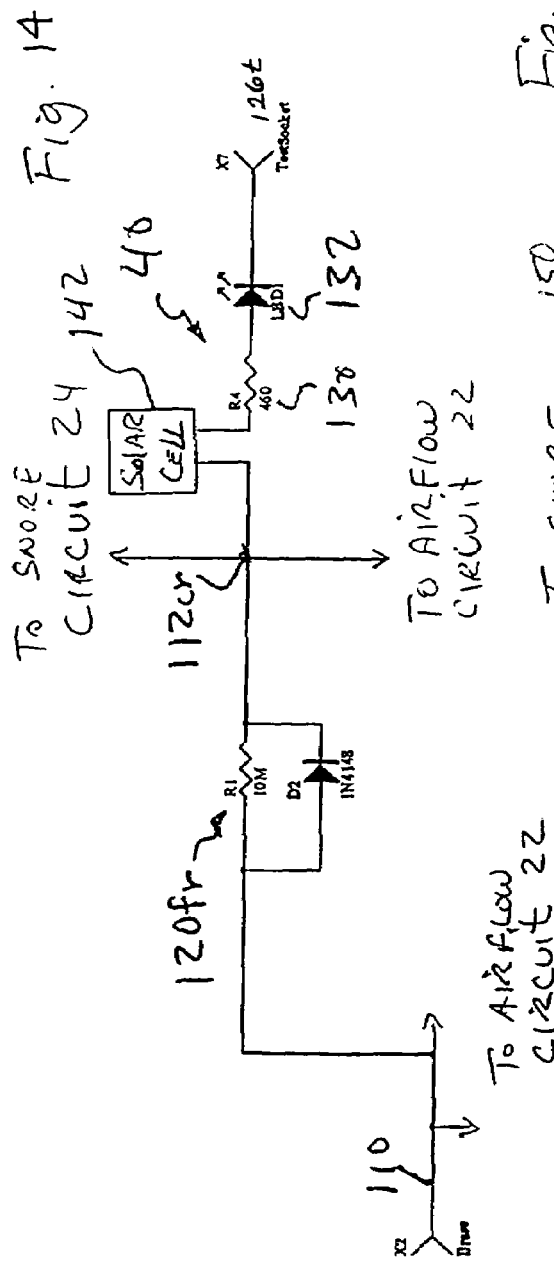
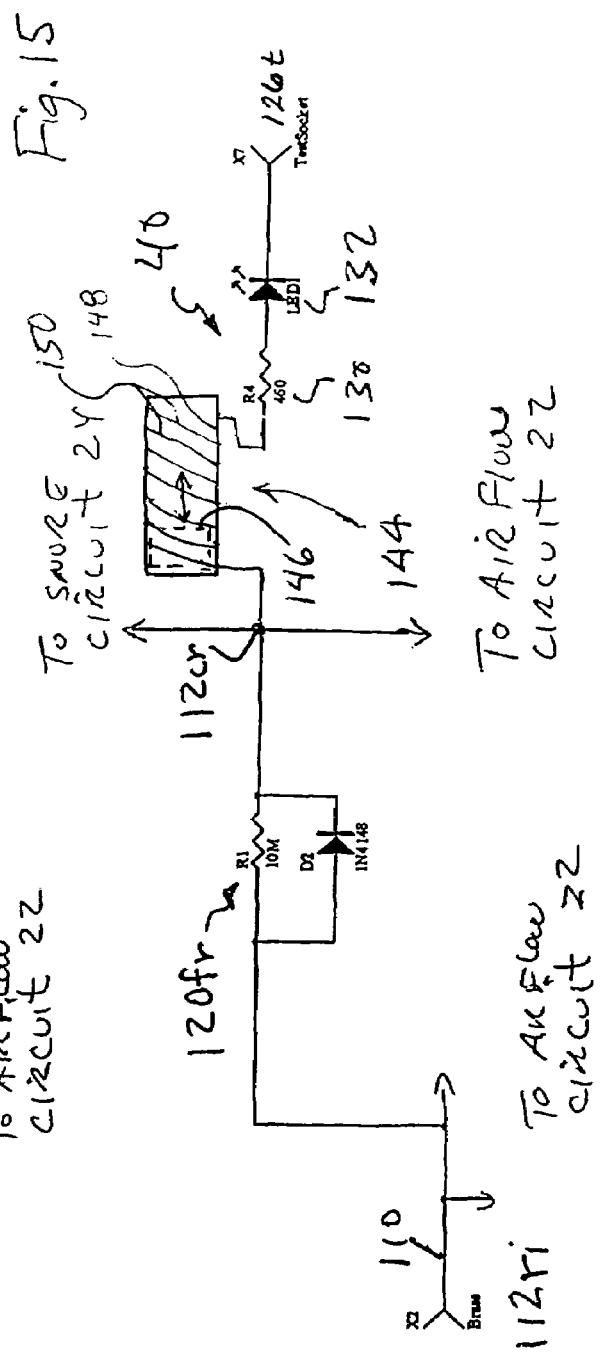

PRESSURE SENSING DEVICE WITH TEST CIRCUIT

FIELD OF THE INVENTION

The present invention relates to a pressure sensing device for measuring respiratory air wave and airflow information during a sleep diagnostic session and processing the acquired air wave and airflow breathing information for input to conventional polysomnography equipment. To facilitate ease of use, the pressure sensing device is equipped with an internal test circuit which allows testing of the circuitry of the pressure sensing device prior to use of the same.

BACKGROUND OF THE INVENTION

A pressure sensing device is currently available from Pro-Tech Services, Inc. of Mukilteo, Wash. This pressure sensing device is used during a sleep diagnostic session to detect changes in respiratory air pressure and/or airflow to confirm whether or not a patient is breathing and to gather other breathing information from the patient. However, before this, as well as other, pressure sensing devices can be utilized during a sleep diagnostic session, it is generally necessary to test the electrical leads for the pressure sensing device to insure that all of the electrical leads are, in fact, operational and not faulty. Due to the relatively small voltage that is utilized by the pressure sensing device, e.g., the pressure sensing device typically operates on millivolts, and due to the fact that noise is typically generated in and by such pressure sensing devices, the test circuitry for such pressure sensing devices can be fairly expensive, e.g., costing hundreds of dollars or so.

In addition, conventional test circuitry typically is completely separate from the pressure sensing device and this leads to further difficulties such as the test circuitry being either misplaced, lost, may have insufficient electrical power, etc., thereby rendering it difficult to test the pressure sensing device prior to use of the same.

SUMMARY OF THE INVENTION

Wherefore, it is an object of the present invention to overcome the above noted drawbacks of the prior art.

Another object of the present invention is to provide test circuitry which is integrated directly into the pressure sensing device and readily allows the electrical circuits, of the pressure sensing device, to be quickly and conveniently tested prior to use of the pressure sensing device and confirm that the pressure sensing device is fully operational prior to use thereof.

A further object of the present invention is to provide a pressure sensing device which can be powered by a solar cell to eliminate dependency upon a battery for powering the pressure sensing device.

Yet another object of the present invention is to provide test circuitry in which the integrity of all of the internal circuitry of the pressure sensing device can be quickly and conveniently checked, by utilizing an internal battery powered circuit, to insure that there is adequate electrical conductivity for all of the internal circuitry and that none of the internal circuits is open, e.g., no electrical short is contained in any of the internal circuits.

A still further object of the present invention is to provide a piezoelectric crystal or piezo transducer within the test circuitry, for solely powering the test circuitry, to eliminate the need for a battery powering the test circuitry of the pressure sensing device when checking the electrical conductivity of the electrical leads.

Still a further object of the present invention is to provide a strain gauge arrangement which eliminates the need for utilizing a battery for powering the test circuitry, to insure that there is adequate electrical conductivity for all of the internal circuitry and that none of the internal circuits is open, e.g., no electrical short is contained in any of the internal circuits.

Yet another object of the present invention is to color code each pair of electrical leads, for each internal circuit of the pressure sensing device, to facilitate quick and accurate identification of the same. Preferably the pair of electrical leads, electrically coupled to the respiratory airflow detection circuit, are color coded a first color scheme, such as blue, red, yellow, black, grey, green, etc., which matches the color coding scheme of the airflow Hi/Lo switch for the respiratory airflow detection circuit and/or an area or border around the airflow Hi/Lo switch, while a second pair of electrical leads, electrically coupled to the respiratory snore detection circuit, are color coded a different second color scheme, such as blue, red, yellow, black, grey, green, etc., which matches the color coding scheme of the snore Hi/Lo switch for the respiratory snore detection circuit and/or an area or border around the snore Hi/Lo switch to facilitate the ease of use by an end user.

Another object of the present invention is to facilitate ease of connection of a nasal cannula to the pressure sensing device whereby the pressure sensing device remains flat on a support surface, such as a table, night stand, counter, etc., to facilitate actuation or switching of the airflow and snore Hi/Lo switches, located on the top surface of the pressure sensing device, in a stable manner for controlling operation of the respiratory airflow detection circuits and the respiratory snore detection circuitry.

The present invention relates to a pressure sensing device for coupling to a cannula and receiving respiratory breathing information from a patient to be monitored, the pressure sensing device comprising: an exterior housing accommodating an input port, the input port being coupled to the cannula for receiving the respiratory breathing information from the patient to be monitored: the exterior housing accommodating a respiratory snore detection circuit for processing the received respiratory breathing information from the patient and outputting, via a pair of snore electrical leads, a signal indicative of sensed snoring of the patient; the exterior housing accommodating a respiratory airflow detection circuit for processing the received respiratory breathing information from the patient and outputting, via a pair of airflow electrical leads, a signal indicative of sensed airflow of the patient; and an internal test circuit for testing an integrity of the airflow electrical leads and the snore electrical leads prior to use of the pressure sensing device for ensuring that the airflow and the snore electrical leads are operational.

The present invention also relates to a method of using a cannula to receive respiratory breathing information from a patient to be monitored, the method comprising the steps of: using a pressure sensing device comprising an exterior housing accommodating an input port, coupling the input port to the cannula for receiving the respiratory breathing information from the patient to be monitored; accommodating a respiratory snore detection circuit within the exterior housing for processing the received respiratory breathing information from the patient and outputting, via a pair of snore electrical leads, a signal indicative of sensed snoring of the patient; accommodating a respiratory airflow detection circuit within the exterior housing for processing the received respiratory breathing information from the patient and outputting, via a pair of airflow electrical leads, a signal indicative of sensed airflow of the patient; and testing an integrity of the airflow electrical leads and the snore electrical leads via an internal test circuit, prior to use of the pressure sensing device, to ensure that the airflow and the snore electrical leads are operational.

BRIEF DESCRIPTION OF THE DRAWINGS

The invention will now be described, by way of example, with reference to the accompanying drawings in which:

FIG. 1 is a diagrammatic perspective view showing connection of the pressure sensing device to a nasal cannula, for collection of from a patient, and coupled to diagnostic equipment for inputting the processed and collected information to diagnostic equipment for analysis;

FIG. 2 is a diagrammatic perspective view of a first embodiment of a pressure sensing device, according to the present invention, having both airflow and snore detection circuits;

FIG. 2A is a front elevational view of the pressure sensing device of FIG. 2;

FIG. 2B is a side elevational view of the pressure sensing device of FIG. 2 with a separate replaceable filter component connected to the input port;

FIG. 3 is a diagrammatic perspective view of a second embodiment of a pressure sensing device, according to the present invention, having both internal respiratory airflow and snore detection circuits;

FIG. 3A is a front elevational view of the pressure sensing device of FIG. 3;

FIG. 12 is a diagrammatic diagram of another embodiment of the test circuit;

FIG. 13 is a diagrammatic diagram of a still further embodiment of the test circuit;

FIG. 14 is a diagrammatic diagram of a test circuit powered by a solar cell; and FIG. 15 is a diagrammatic diagram of a test circuit powered by a physically activated electrical generator.

DETAILED DESCRIPTION OF THE INVENTION

Figure 4A:
FIG. 4A is a diagrammatic drawing of a portion of unfiltered periodic respiration pressure waveform representing normal inspiration and expiration of a patient.

Turning now to FIGS. 1-5, a detailed description concerning a first embodiment of the pressure sensing device 2 of the present invention will now be provided. The pressure sensing device 2 of the present invention is generally a two output channel device which can be used to acquire respiratory (low) air pressure wave information and respiratory (low) airflow information (both of which are herein after collectively referred to as "breathing information 4") via a conventional nasal cannula 60 worn by a patient P during a sleep diagnostic session or some other patient monitoring session. The nasal cannula 60 has a pair of spaced apart nares 65, 67 and preferably at least one or possibly a spaced apart mouthpiece lumens 69, 69' to facilitate detection of respiratory air pressure waves and/or respiratory airflow in the event that the patient P breathes through his or her mouth. The nasal cannula 60 collects or acquires the breathing information 4, generated by breathing and/or snoring of the patient P, from the nostrils and/or mouth of the patient P being monitored. The pressure sensing device 2 is able to convert the acquired respiratory breathing information 4, received by one or both of the nares 65, 67 of the cannula 60 and/or one or both of the mouthpiece lumens 69, 69' (if present) of the nasal cannula 60, into at least two separate electrically signals 110 which can be separately processed by the pressure sensing device 2 and outputted, as two separately processed electrical signals, to diagnostic equipment 9 such as polysomnography equipment for measurement or analysis in a conventional fashion.

The acquired breathing information 4 is channeled or directed along a pair of separate flexible conduits or tubing 74, 76 (one connected to each outlet 73, 74 of the nasal cannula 60), which eventually combine with one another, at a coupling device 78, into a common flexible conduit or tubing 80 (see FIG. 1). A first end of the common flexible conduit or tubing 80 is connected to the opposite end of the coupling device 78 while a second opposed end of the common flexible conduit or tubing 80 is connected to an input port 6 of the pressure sensing device 2, to supply the acquired breathing information 4 from the patient P to the pressure sensing device 2.

Typically, a filter 84 is provided somewhere along the common flexible conduit or tubing 80 or at the interface between the common flexible conduit or tubing 80 and the pressure sensing device 2 to prevent moisture, or other particulate matter, for flowing or being conveyed from any one of the openings of the nasal cannula 60 into the pressure sensing device 2. Preferably, the filter 84 is either integral with a connector member 82, which facilitates connection of the common flexible conduit or tubing 80 of the nasal cannula 60 with the input port 6 of the pressure sensing device 2, or the filter 84 is separate replaceable component 63 (see FIGS. 2B and 3B) which facilitates coupling of the connector member of the common flexible conduit or tubing 80 to the input port 6 of the pressure sensing device 2. That is, the separate replaceable filter component 63 has a female luer connector 81, at one end thereof, for connection to the input port 6 of the pressure sensing device 2, and has a male luer connector 90, at an opposite end thereof, for connection with the female luer connector 82 of the common flexible conduit or tubing 80 of the nasal cannula 60. The separate replaceable filter component 63 facilitates repeated use thereof, i.e., the separate replaceable filter component 63 is only replaced when the internal filter 84 is sufficiently contaminated.

The acquired breathing information 4, e.g., the respiratory air pressure wave information and/or the respiratory airflow information, is received by the input port 6 and conveyed to a piezoelectric crystal or a piezo transducer (hereinafter "piezo transducer 8") of the pressure sensing device 2 and processed into two separate signals, and each signal is separately processed as a voltage and attenuated and filtered by the respiratory airflow detection circuit 22 and respiratory snore detection circuit 24 of the pressure sensing device 2, as will be discussed below in further detail, prior to outputting such processed output signals to conventional diagnostic equipment 9 such as polysomnography equipment for example. As the diagnostic equipment 9 does not form any part of the present invention, per se, a further detail discussion concerning the same will not be provided herein.

As can be seen in FIGS. 2, 2A, 2B, 3, 3A and 3B of the drawings, the pressure sensing device 2 generally comprises a rigid exterior housing 10 which has an opposed generally planar top and bottom surfaces 14, 12 and a generally contoured and curved exterior side wall 16. A pair of spaced apart "Hi/Lo" switches 18, 20, such as an airflow "Hi/Lo" switch 18 and a snore "Hi/Lo" switch 20, are located on the top surface 14 of the pressure sensing device 2 (in FIGS. 2-2B) or in the side wall or surface 16 (in FIGS. 3 and 3A), and each switch 18, 20 has two setting or positions, namely, a Hi (high) position and a Lo (low) position. When either "Hi/Lo" switch 18, 20 is in its Lo (low) position, the amplitude of the output signal is generally one fourth of the amplitude of the output signal for the Hi (high) position. Conversely, when either "Hi/Lo" switch 18, 20 is in its Hi (high) position, the amplitude of the output signal is generally four times the amplitude of the output signal for the Lo (low) position. The airflow "Hi/Lo" switch 18 controls the internal circuit relating to respiratory airflow detection circuit 22 while the snore "Hi/Lo" switch 20 controls the internal circuit relating to the respiratory snore detection circuit 24. A further detailed description concerning the respiratory airflow detection circuit 22 and the respiratory snore detection circuit 24 will be provided below. The housing 10 also contains a light emitting diode 132 which is associated with a built-in test circuit 40, discussed below in further detail, to confirm whether or not the electrical leads 26, 28, 30 and 32 are in fact operational. That is, there is continuity for each of the electrical leads 26, 28, 30 and 32, e.g., there is not any electrical short contained in any of the electrical leads.

The planar bottom surface 12 facilitates locating and supporting of the pressure sensing device 2 on a desired support surface S such as a table, a counter, a night stand, a dresser, etc., so that the pressure sensing device 2 remains positioned on such support surface S in a very stable manner with the pair of "Hi/Lo" switches 18, 20 facing upward so as to be readily accessible by an end user (see FIG. 2B, for example).

To facilitate receiving the acquired breathing information 4 from the patient P being monitored, the input port 6 is at least partially generally formed in the top surface 14 of the pressure sensing device 2 (see FIGS. 2-2B). It is to be appreciated that the input port 6 may also be connected with an upper portion of the side wall 16 of the housing 10 (see FIGS. 3-3B). An exterior surface of the remote free end of the input port 6 is provided with a conventional male luer style coupling which facilitates a releasable locking engagement of the input port 6 with a mating conventional female luer style coupling carried by, for example, a filter 84 which is connected to a free end of the common conduit or tubing 80 connected with the nasal cannula 60 and positioned on the patient P being monitored to acquire breathing information 4 and supply the same to the pressure sensing device 2. The filter 84 prevents any moisture, or other undesired particular matter which may flow along the tubing 80, from reaching and contaminating the pressure sensing device 2.

The acquired respiratory breathing information 4, received from the patient P to be monitored, is received by and inputted to the pressure sensing device 2 via the input port 6. A shown in this embodiment, a central axis for the input port 6, of the pressure sensing device 2, generally projects slightly, e.g., from about 0.1 to about 0.5 inches or so, from the bottom surface 12 of the housing 10 and extends away from the housing 10 for a distance of about to 0.3 about 1.5 inches or so, generally parallel to both the top and bottom surfaces 14, 12 of the housing 10.

One aspect of the present invention is that the input port 6, for engaging with the filter 84 carried by the leading end of the common tubing 80 or supported by the input port 6, either extends generally parallel to the bottom surface 12 or is spaced sufficiently away from the bottom surface 12 of the housing 10 such that the filter 84, carried by the leading free end of the flexible common conduit or tubing 80 of the nasal cannula 60, when connected to the input port 6 of the pressure sensing device 2, will remain sufficiently spaced from the support surface S, supporting the pressure sensing device 2, such that the bottom surface 12 of the housing 10 will always remain flush with and in constant and continuous intimate contact with the support surface S (see FIG. 2B). That is, the bottom surface 12 of the pressure sensing device 2 will always remains in the contact with and lie generally in a plane defined by the support surface S whereby the pressure sensing device 2 remains in a stable position which facilitates actuation of the airflow and snore "Hi/Lo" switches 18, 20, by an end user, during use of the pressure sensing device 2.

Figure 3B:
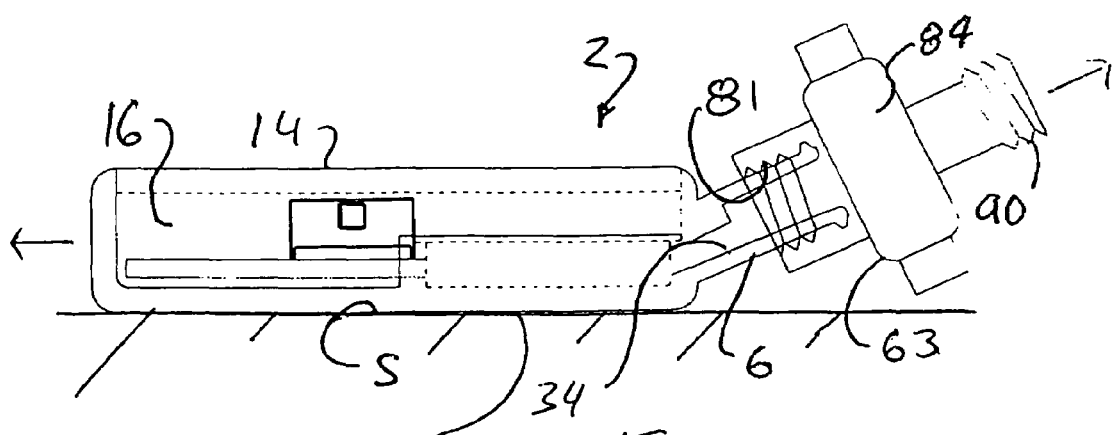
FIG. 3B is a side elevational view of the pressure sensing device of FIG. 3 with a separate replaceable filter component connected to the input port.

Alternatively, as shown in FIGS. 3, 3A and 3B, the input port 6 of the pressure sensing device 2 can be connected to a front side wall 16 of the housing 10, at a position adjacent the bottom surface 12, and extend therefrom at a desired angle or be sufficiently inclined with respect to the bottom surface 12 and have a sufficient length such that the filter 84 contained within the connector 82, carried by the leading free end of the flexible common conduit or tubing 80 connected with the nasal cannula 60 or coupled to the input port 6, will remain sufficiently spaced from the support surface S, supporting the pressure sensing device 2, so that the bottom surface 12 of the housing 10 will always remain flush with and in intimate contact with the support surface S (see FIG. 3B). That is, the bottom surface 12 of the pressure sensing device 2 will always remains in the contact with and lie generally in the plane defined by the support surface S so that the pressure sensing device 2 remains in a horizontal and stable position which facilitates actuation of the airflow and/or the snore "Hi/Lo" switches 18, 20 during use of the pressure sensing device 2.

While the input port 6 of the housing 10 (see FIGS. 3, 3A and 3B) is shown as projecting from the end wall of the housing 10 at an angle of between about 140 to about 170 degrees, preferably about 155 degrees or so, it is to be appreciated that the angle at which the input port 6 projects from the housing 10 can be varied, as desired, to suit any particular application. It is preferable that the input port 6 has a sufficient length and extends at an angle which is sufficient to ensure that the filter 84 is totally spaced from the support surface S so that the bottom surface 12 of the housing 10 is able to lie flush and within the plane defined by the support surface S as such arrangement leads to the stability of the pressure sensing device 2 during use thereof.

As noted above, the nasal cannula 60 (see FIGS. 6-11) has a pair of spaced apart nares 65, 67 which are insertable in a conventional manner, during use, in respective nostrils of the patient P to be monitored. As noted above, the nasal cannula 60 may also including one or more mouthpiece lumens 69, 69' for positioning adjacent a mouth of the patient P being monitored so as to provide input signals to the pressure sensing device 2 in the event the patient P being monitored is a mouth breather, or alternates breathing between his or her nose and mouth. The one or more lumens 69, 69', for position adjacent a mouth of the patient P being monitored, will facilitate acquiring breathing information 4 from the patient P, for monitoring respiratory airflow and/or respiratory snoring of the patient P being monitored, in the event of mouth breathing by the patient P.

One or more of the nares 65 and/or 67, of the nasal cannula 60, may be provided with at least one secondary inlet/outlet hole, aperture or opening 35, 36, 37, 38 in a side wall of the nare 65, 67, to provide a secondary inlet or outlet for the nare 65, 67 in the event that the primary inlet/outlet opening 62, 64 in the end surface or wall of the nare 65, 67 becomes partially or completely clogged, blocked, obstructed or occluded for some reason during use of the nasal cannula 60. The secondary inlet/outlet hole, aperture or opening 35, 36, 37, 38 will assist the nare 65, 67 of the nasal cannula 60 with still being able to receive breathing information 4 from the patient P, for detecting the airflow and/or snoring of the patient P being monitored, in the event that the primary inlet/outlet opening 62, 64 becomes clogged, blocked, obstructed or occluded for some reason.

An internal passage 34 of the input port 6 communicates with the piezo transducer 8 so as to supply the acquired breathing information 4 thereto and the acquired and supplied breathing information 4 moves, vibrates and/or excites the piezo transducer 8. The piezo transducer 8 outputs an electrical signal, depending upon the extend or degree that the piezo transducer 8 is excited by the acquired and supplied breathing information 4. This electrical signal is then divided into two separate signals and each signal is inputted to one of the internal circuits 22 and 24. That is, a first signal is inputted to the respiratory airflow detection circuit 22 and the other second signal is inputted to the respiratory snore detection circuit 24. Each inputted signal flows through the respective circuits 22 and 24 and is suitably processed and an output signal, from the respiratory airflow detection circuit 22, is then transmitted by a pair of color coded respiratory airflow electrical leads 26 and 28 while an output signal, from the respiratory snore detection circuit 24, is transmitted by a pair of color coded respiratory snore electrical leads 30 and 32. The remote ends of the pair of airflow and snore electrical leads 26, 28, 30 and 32 can then be coupled or connected, in a standard fashion, to conventional sleep diagnostic equipment 9, such as a polysomnography equipment, which can then be utilized to collect, monitor, record and/or plot, as necessary or desired, the airflow characteristics and/or the snore characteristics of the patient P being monitored.

Figure 4B:
FIG. 4B is a diagrammatic drawing of a portion of filtered periodic respiration pressure waveform representing only respiration of the patient.
Figure 4C:
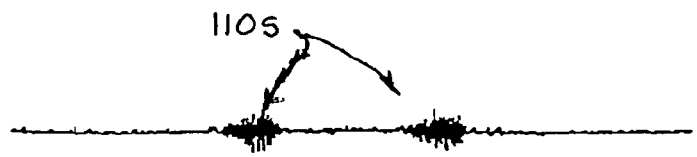
FIG. 4C is a diagrammatic drawing of a portion of filtered periodic respiration pressure waveform representing only snoring of the patient.
Figure 4:
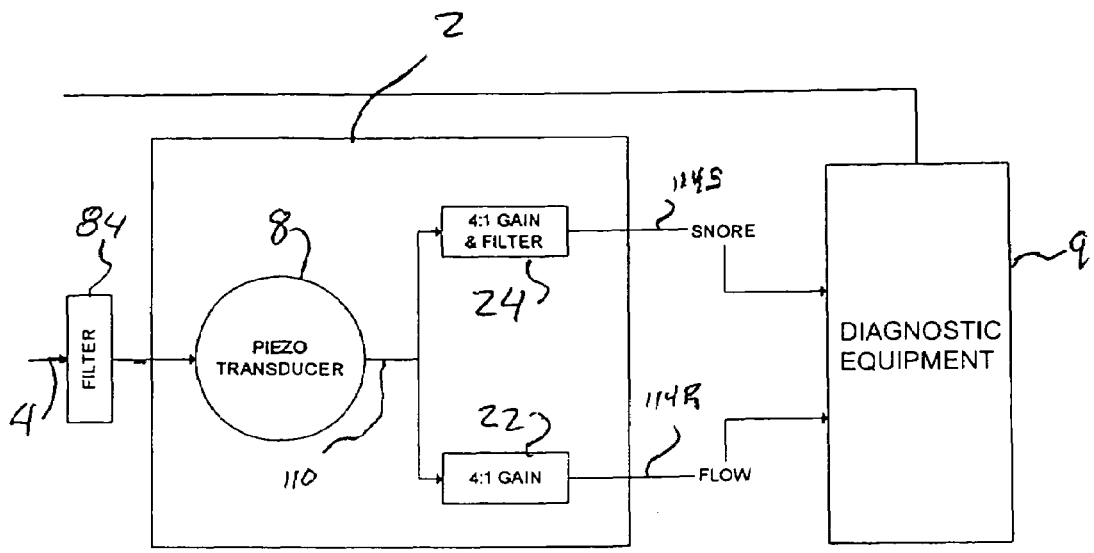
FIG. 4 is a diagrammatic diagram of the internal circuitry showing splitting of the received airflow signal into two signals, a first for the airflow detection circuit and a second signal for the snore detection circuit.
Figure 5:
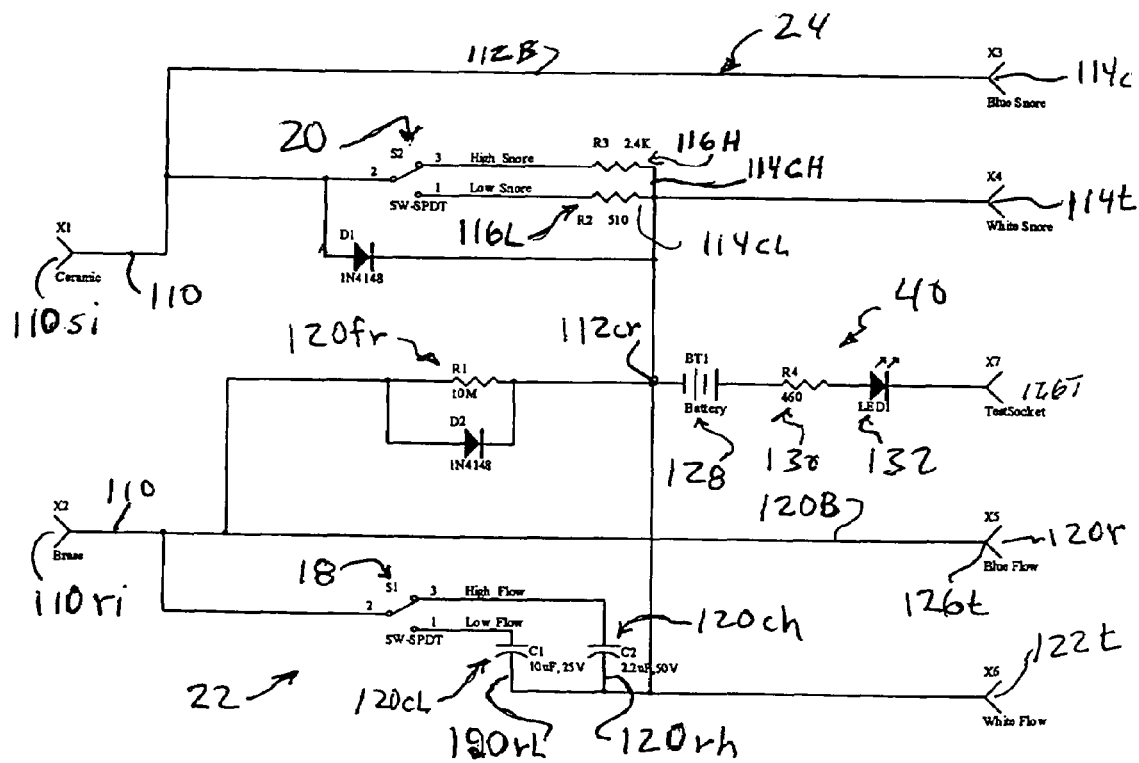
FIG. 5 is a diagrammatic diagram of the internal circuitry showing the airflow detection circuit, the snore detection circuit and the test circuit.

With reference to FIGS. 4 and 5, a detailed description concerning the respiratory snore detection circuit 24 will now be provided. Referring first to FIG. 4, therein is presented a diagrammatic representation of the pressure sensing device 2 which includes the input port 6, which is connected with a cannula 60 that acquires breathing information 4, e.g., input respiratory airflow and/or respiratory snore information from the patient P which is representative of the respiration airflow sensed by the inlet/outlet openings 35, 36, 37, 38, 62, 64, 83 and/or 87 (i.e., the openings in either the nares 65, 67 and/or the mouthpiece lumens 69, 69'). The acquired breathing information 4 passes through the filter 84, prior to communicating with the piezo transducer 8. The piezo transducer 8, in turn, is responsive to the acquired breathing information 4 and generates an input respiration signal 110 that correlates to the respiration airflow of the patient P sensed by the inlet/outlet openings 35, 36, 37, 38, 62, 64, 83 and/or 87 of the cannula 60.

As illustrated in FIGS. 4A, 4B and 4C, the respiration airflow of the patient P, sensed by the inlet/outlet openings of the cannula 60, includes a generally periodic respiration airflow representing normal inspiration or inhalation and expiration or exhalation of the patient P and may also include a component representing snoring when the patient P is asleep, such as for the second and third breathing cycles. The input respiration signal 110 correspondingly includes a respiration component 110r in the general frequency range of about 5-15 Hz and represents the normal inspiration or inhalation and expiration or exhalation of the patient P and may also include a snoring component 110s in the general frequency range of from about 10 Hz to 300 Hz which represents snoring respiration of the patient P.

FIG. 5 is a diagrammatic representation of the respiratory airflow detection circuit 22, the respiratory snore detection circuit 24, and the test circuit 40 where the drawing illustrates that the input respiration signal 110 from the piezo transducer 8 is connected to a snore input 110si as the input to the respiratory snore detection circuit 24 for use in generating a composite respiratory snore output signal 114c.

As illustrated, composite respiratory snore output signal 114c is essentially the input respiration signal 110, that is, includes a respiration component 110r and possibly a snoring component 110s, but is adjusted for amplitude by the respiratory snore detection circuit 24. For this purpose, the respiratory snore detection circuit 24 comprises a snore "Hi/Lo" (amplitude selection) switch 20 connected from snore input 110si that selectably connects snore input 110si, and thus the connection to the snore output signal 114c through a direct path 112b to a circuit reference point 112cr through either a high snore composite resistance 116h, to form a high composite respiratory snore output signal 114ch, or through a low snore composite resistance 116l, to form a low composite respiratory snore output signal 114cl. As will be understood by those of skill in the arts, the piezo transducer 8 not only generates the input respiration signal 110 but also has a characteristic internal impedance, usually capacitive. The combination of the internal capacitive impedance of the piezo transducer 8 with the selected one of the high snore composite resistance 116h and the low snore composite resistance 116l effectively from a voltage divider circuit, thereby controlling the amplitude of snore output signal 114c.

In a present embodiment, the resistance values of the high composite resistance 116h and the low composite resistance 116*l* are selected, in combination with the internal impedance of the piezo transducer 8, so that the output amplitude of the low composite respiratory snore output signal 114*cl* is approximately one fourth of the amplitude of the high composite respiratory snore output signal 114*ch*.

With reference to FIGS. 4 and 5, a detailed description concerning the respiratory airflow detection circuit 22 will now be provided.

As further illustrated in those Figures, the circuitry of pressure sensing device 2 further includes a respiratory airflow detection circuit 22 for also receiving the input respiration signal 110, from the piezo transducer 8, via a respiratory input 110*ri* and generating a respiration airflow output signal 120*r* wherein respiration airflow output signal 120*r* includes a respiration component 110*r*, but does not include a snoring component 110*s*, and is adjusted for amplitude. For this purpose, the respiratory airflow detection circuit 22 comprises the airflow "Hi/Lo" (amplitude selection) switch 18 that selectably connects respiratory input 110*ri*, and thus the connection to respiration airflow output signal 120*r*, to reference point 112*cr* through either a high respiration airflow capacitance 120*ch* or a low respiration airflow capacitance 120*cl* to provide respectively either a high respiration airflow output signal 120*rh* or a low respiration airflow output signal 120*rl*. The high respiration airflow capacitance 120*ch* or the low respiration airflow capacitance 120*cl* thereby again forms a voltage divider circuit with the capacitive internal impedance of the piezo transducer 8. In addition, a filter resistor 120*fr* is connected in parallel with the high respiration airflow capacitance 120*ch* and the low respiration airflow capacitance 120*cl* to form a filter circuit which filters out the higher frequency components, that is, any snoring component 110*s* in the 10 Hz-300 Hz range, from the input respiration signal 110 so that the respiration airflow output signal 120*r* contains only the respiration component 110*r*.

In a present embodiment, the capacitance values for the high respiration airflow capacitance 120*ch* or the low respiration airflow capacitance 120*cl* are selected, in combination with the values of the filter resistor 120*fr* and the internal capacitive impedance of the piezo transducer 8, so that any snoring component(s) 110*s* of input respiration signal 110, above approximately 10 Hz, are filtered out and so that the amplitude of the low respiration airflow output signal 120*rh* is approximately one fourth of the amplitude of the high respiration signal output 120*rh*.

Since the embodiment of FIGS. 1-5 are passive systems, it is generally not necessary to equip the pressure sensing device 2 with an "on/off" switch. However, in the event that the pressure sensing device 2 is battery operated, then it is desireable to equip the exterior surface of the housing 10 with an "on/off" switch (not shown) for turning on the electrical power for the pressure sensing device 2 either "On" and "Off" as desired.

Another novel aspect of the present invention is that a test circuit 40 is incorporated within the pressure sensing device 2 so that the operator can confirm that the electrical leads for both the respiratory airflow detection circuit 22 and the respiratory snore detection circuit 24 are properly operating. That is, each of the electrical leads 26, 28, 30 and 32 ,for the internal circuitry, has adequate electrical conductivity and there is not an electrical short in any of the electrical leads and the electrical leads do not from part of an "open" circuit. An inherent problem for the test circuit 40 of the pressure sensing device 2 is that each of the respiratory airflow detection circuit 22 and the respiratory snore detection circuit 24 both operate at a very low voltages, e.g., micro volts, and any surrounding or created noise or interference may cause measurement problems. Such noise or interference is to be reduced as much as possible.

With reference now to FIG. 5, a detailed description concerning a first embodiment of the test circuit 40 will now be provided. According to this embodiment, the test circuit 40 is battery operated. It is to be appreciated, however, that instead of utilizing a battery to electrically power the test circuit 40, a solar cell, a strain gauge, a piezo transducer, or a piezoelectric crystal, etc., a could be utilized for powering such test circuit 40 without departing from the spirit and scope of the present invention.

As shown in this Figure, the built-in test circuit 40 generally includes a battery 128, a resistor 130, a light emitting diode 132 and a test output signal 126*t* connected in series from circuit reference point 112*cr* to comprise a test signal source and a test indicator. In this regard, it should be noted that reference connection 114*t* associated with composite respiratory snore output signal 114*c* and reference connection 122*t* associated with respiration airflow output signal 120*r* are all connected to the circuit reference point 112*cr* to provide a reference level for the composite respiratory snore output signal 114*c* and the reference connection 122*t* associated with respiration airflow output signal 120*r*. The test signal output 126*t* may thereby be connected to any of the connections 114*c*, 114*t*, 120*r* or 122*t*, that is, to the outputs and reference connections of either the respiratory snore detection circuit 24 or the input of the respiratory airflow detection circuit 22, with a resulting current flow there through and thus an indicated of a completed circuit which is indicated by illumination of the light emitting diode 132. This facility thereby confirms that there is no "electrical short" in the electrical circuit and that the external lead 26, 28, 30 or 32 is continuous and properly connected with the respective circuit.

To facilitate testing of the electrical leads 26, 28, 30 and 32, preferably the side wall 16 of the housing 10 is provided with a socket, a receptacle or a plug 42 of some sort (see FIG. 2B) which has an electrical contact 44 which forms the test output signal 126*t* of the built-in test circuit 40. The remote free end of each electrical lead 26, 28, 30 and 32 is sequentially brought into contact with the electrical contact 44 to receive the test output signal 126*t* and, assuming that the light emitting diode 132 is illuminated by such contact, such illumination confirms to the end user that the electrical lead 26, 28, 30 or 32 is properly connected with the respective circuit and operational.

To facilitate ease of operation and use by an end user, preferably either the airflow switch 18, for controlling the Hi/Lo operation of the respiratory airflow detection circuit 22, or an area, a perimeter or a border 46 surrounding the airflow switch is color coded a first color (such as blue, red, yellow, black, grey, green, etc.), e.g., blue for example, and the associated two airflow electrical leads 26 and 28 connected with the respiratory airflow detection circuit 22 are also colored that same color scheme, e.g., light blue and darker blue (to facilitate distinguishing the two electrical leads 26 and 28 from one another) for example, so that an end user can quickly and reliably identify which pair of electrical leads 26 and 28 which correspond to the respiratory airflow detection circuit 22. In addition, the snore switch 20, for controlling the Hi/Lo operation of the respiratory snore detection circuit 24, or an area, a perimeter or a border 48 surrounding the snore switch 20 is color coded a second (such as blue, red, yellow, black, grey, green, etc.), e.g., grey for example which is separate and distinct from the first color scheme, and the associated two snore electrical leads 30 and 32 connected with the respiratory snore detection circuit 24 are also colored that same color scheme, e.g., light grey and darker grey (to facilitate distinguishing the two electrical leads 30 and 32 from one another) for example, so that an end user can quickly and reliably identify which electrical leads 30 and 32 which correspond to the respiratory snore detection circuit 24. The use of the two unique color coding schemes, for the two associated pair of electrical leads 26, 28 and 30, 32 and switches 18 and 20 (as well as lighter and darker shades of the same color to assist with distinguishing between the respective electrical leads 26 from 28 and 30 from 32), facilitates ease of set up and use of the pressure sensing device 2 by an end user prior to use thereof. While the above description refers to blue and grey as a suitable color coding scheme for the pressure sensing device 2, it is to be appreciated that a variety of other color coding schemes could also be utilized for use with the present invention.

The length of the snore and airflow electrical leads 26, 28, 30 and 32 can vary, depending upon the particular application. Preferably, the snore and the airflow electrical leads 26, 28, 30 and 32 have a length of a least a few inches to about 36 inches or so, or longer if necessary, to facilitate ease of connection to the desired diagnostic equipment 9.

Figure 6:
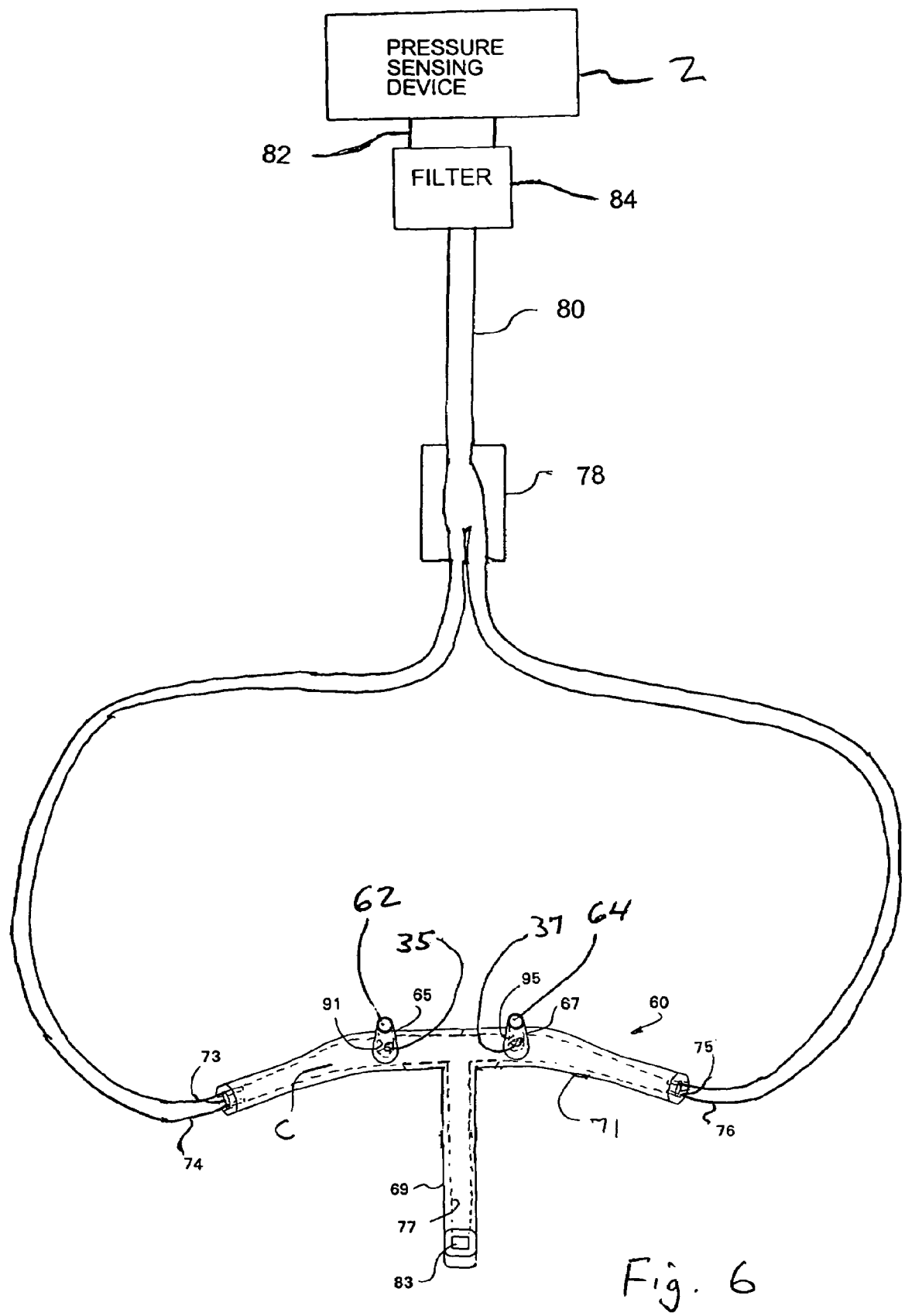
FIG. 6 is a diagrammatic view of a nasal cannula, with a mouthpiece, for connection to the pressure sensing device to facilitate acquiring breathing information of a patient.

With reference to FIG. 6, an embodiment of the cannula will now be discussed. The nasal cannula 60 comprises a single flow path having three separate inlet/outlet openings 62, 64 and 83 to the central internal chamber or compartment C defined by the main body. Each one of the three inlet/outlet openings 62, 64 and 83 to the central internal chamber or compartment C is suitable for acquiring breathing information 4 or possibly monitoring breathing characteristics, detecting pressure, withdrawing or sampling an exhalation gas(es) from the patient nostril (e.g., sampling end tidal $CO_2$ in the exhaled gases of a patient), measuring differential air flow along the tubing connect to the cannula, supplying a treating gas to a patient, etc., both via either a nostril or the mouth of a patient. The central chamber or compartment C of the main body 71 of the cannula 60 is in constant and continuous communication with an inlet/outlet opening 83, formed in end surface of the mouthpiece 69, via a gas passageway 77 in the mouthpiece 69 and also in constant and continuous communication with the inlet/outlet opening 62, formed in end surface of the first nare 65, and the one or more secondary inlet/outlet opening(s) 35 via a gas passageway 91 in the first nare 65 and in constant and continuous communication with the inlet/outlet opening 64, formed in end surface of the second nare 67, and the one or more secondary inlet/outlet opening(s) 37 via a gas passageway 95 in the second nare 67. In addition, the central chamber or compartment C of the main body 71 also communicates with first and second opposed chamber end openings 73, 75 of the cannula 60. As a result of this arrangement, each one of these inlet/outlet openings 62, 64 and 83 can facilitate preforming acquiring breathing information 4, monitoring breathing of a patient via the mouth and/or the nose, sampling the end tidal $CO_2$ content in the exhaled breath of a patient via the mouth and/or the nose to determine the patient's $CO_2$ concentration level in the blood, measuring differential air flow along the tubing connect to the cannula, supplying a treating gas to a patient via the mouth and/or the nose, detecting changes in pressure air flow, or detecting apnea via the mouth and/or the nose, etc.

The first conduit or tubing 74 is connected to the first end chamber opening 73 while the first end of a second conduit or tubing 76 is connected to a second chamber end opening 75. The opposed second ends of the first and second conduits or tubings 74 and 76 are connected to a coupling device 78 which couples the first and second conduits or tubings 74 and 76 to a common conduit or tubing 80 which is also connected to the coupling device 78. The opposite end of the common conduit or tubing 80 typically has a luer connector 82 which is either coupled to a filter 84, prior to engaging with the pressure sensing device 2 or, preferably, the filter 84 may be incorporated into the conventional luer connector 82 and this unitary structure will then facilitate coupling of the nasal cannula 60 to the pressure sensing device 2 as discussed above. The first and second conduits or tubings 74 and 76 each have a length of about 8 inches to about a 24 inches or so and preferably have a length of about 15 to 25 inches or so while the common conduit or tubing 80 typically has a length of about 3 feet to about 10 feet, preferably a length of about 5 to 7 feet or so.

Figure 7:
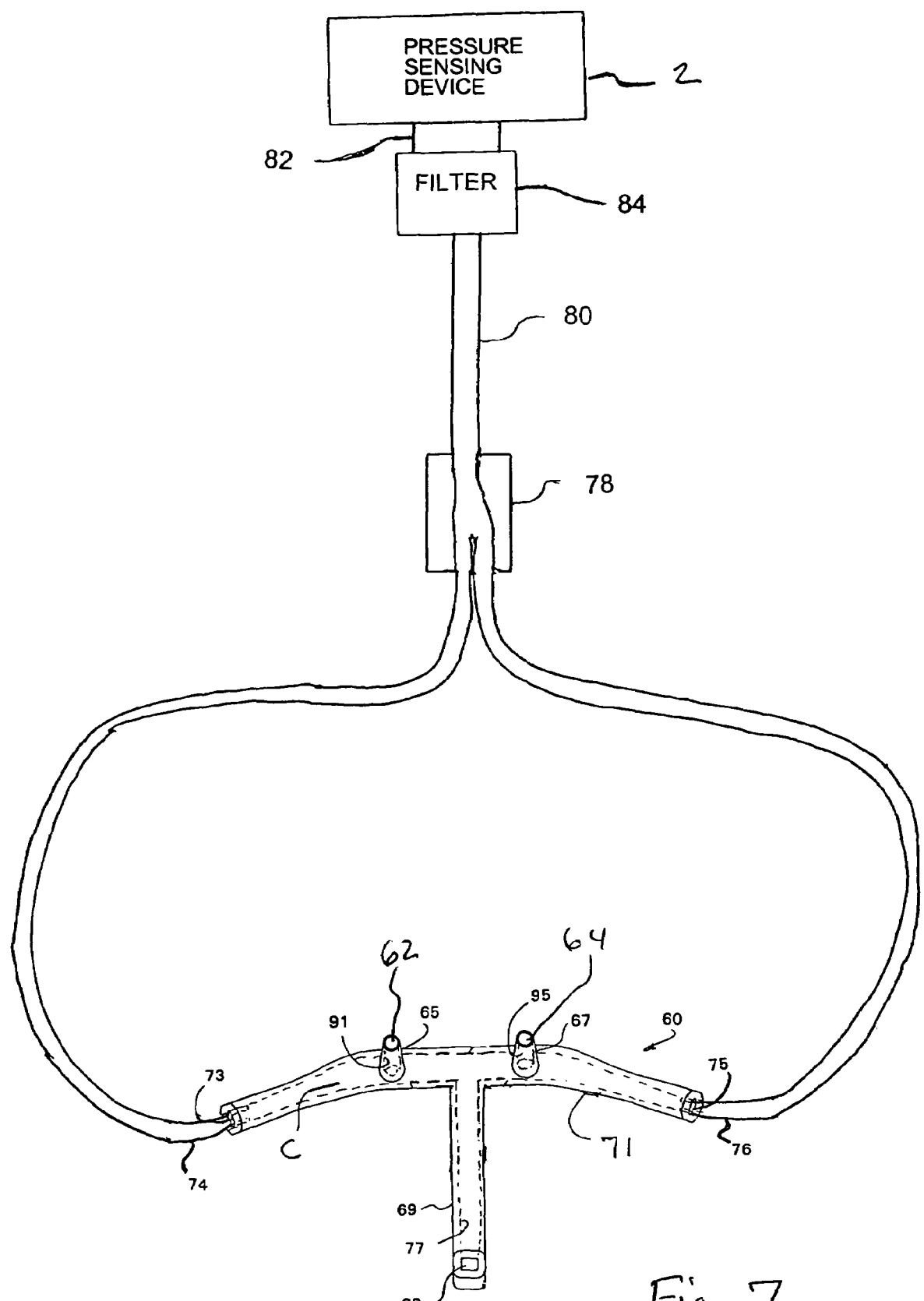
FIG. 7 is a diagrammatic view of a nasal cannula, with a mouthpiece but without any secondary openings in the nares, for connection to the pressure sensing device to facilitate acquiring breathing information of a patient.

With reference to FIG. 7, another embodiment of the cannula will now be discussed. As this embodiment is very similar to the embodiment of FIG. 6, identical reference numerals will given to identical elements and only the differences between this embodiment and the previous embodiment will be discussed in detail.

The only significant difference between this embodiment of the cannula and the embodiment of FIG. 6 is the elimination of all of the secondary inlets/outlets openings 35 and 37 adjacent the tip so that each nare 65 and 67 only has a primary flow passage into and out of the nare but not any secondary flow passage in the event that the primary inlets/outlets openings 62, 64 of the nares 65, 67 become either partially or fully occluded, blocked, clogged or otherwise obstructed during use of the nasal cannula. That is, flow into and out of the nares 65, 67 can only occur via the primary inlet/outlet openings 62, 64 formed in the nares 65, 67, respectively.

Figure 8:
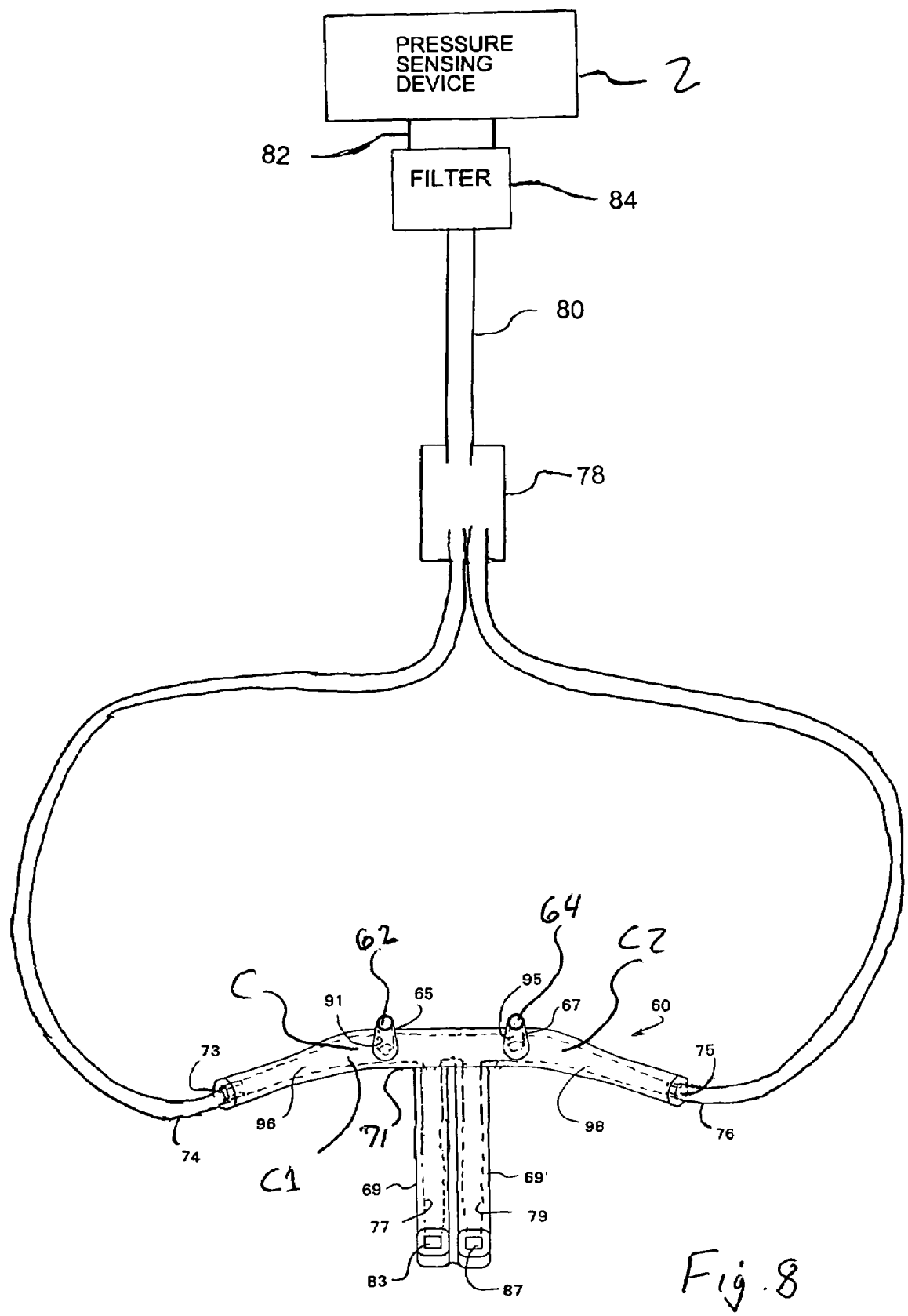
FIG. 8 is a diagrammatic view of an undivided nasal cannula, with a pair of integral mouthpieces but without any secondary openings in the nares, for connection to the pressure sensing device to facilitate acquiring breathing information of a patient.

With reference to FIG. 8, another embodiment of the cannula will now be discussed. As this embodiment is very similar to the embodiment of FIG. 7, identical reference numerals will given to identical elements and only the differences between this embodiment and the previous embodiment will be discussed in detail.

The only significant differences between this embodiment and the embodiment of FIG. 7 is the inclusion of a second integral mouthpiece 69'. As a result of this arrangement, the first and second internal gas passageways 77, 79 and the first and second gas passageways 91 and 95 in the nares 65 and 67 and all of the openings 62, 64, 73, 75, 83 and 87, are in constant and continuous communication with one another.

Figure 9:
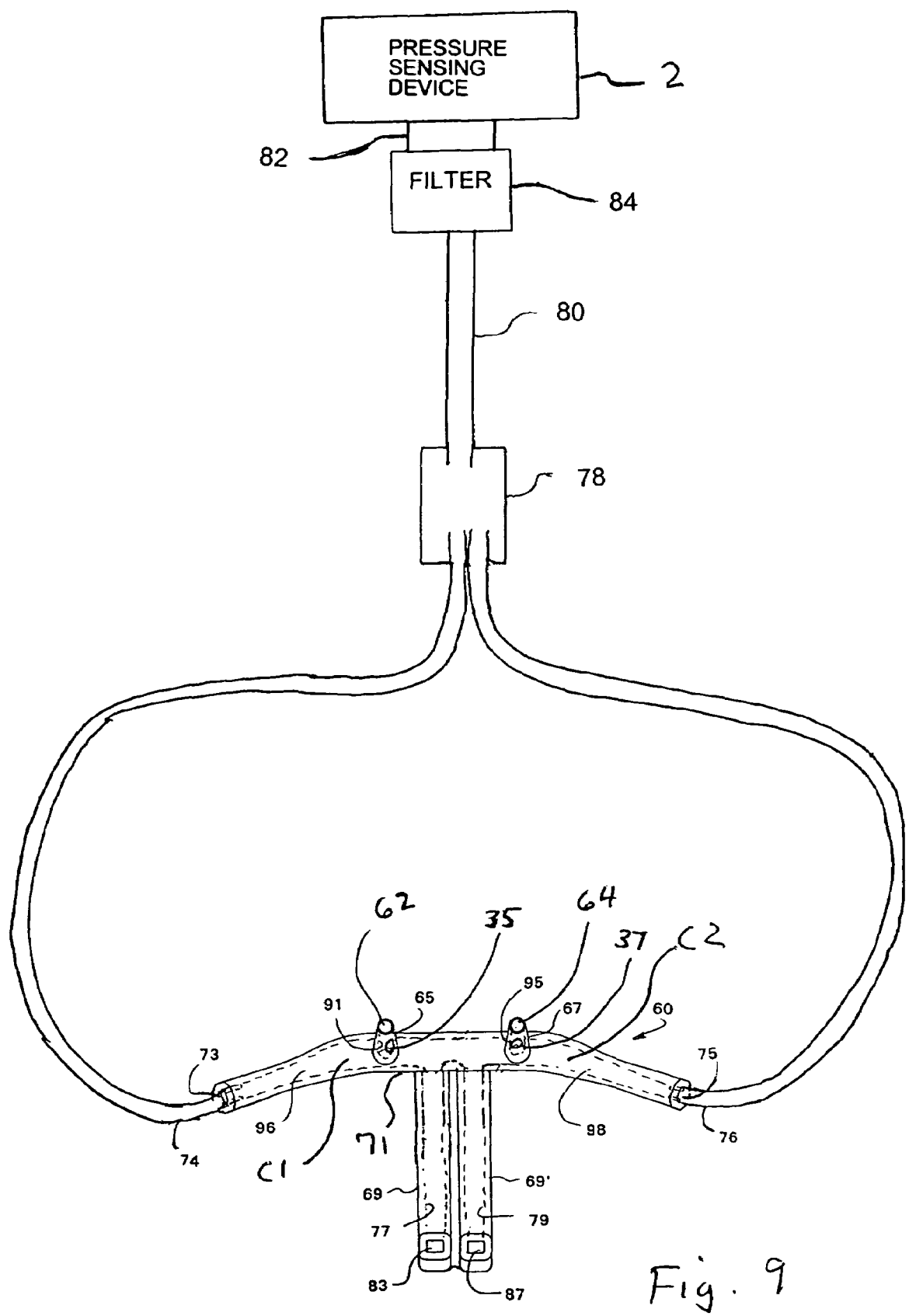
FIG. 9 is a diagrammatic view of an undivided nasal cannula, with a pair of integral mouthpieces and with nares having secondary openings therein, for connection to the pressure sensing device to facilitate acquiring breathing information of a patient.

With reference to FIG. 9, yet another embodiment of the cannula will now be discussed. As this embodiment is very similar to the embodiment of FIG. 8, identical reference numerals will given to identical elements and only the differences between this embodiment and the previous embodiment will be discussed in detail.

The only significant difference between this embodiment and the embodiment of FIG. 8 is the inclusion of at least one, and preferably a pair of secondary inlets/outlets openings 35 and 37, adjacent the tip of each one of the nares 65, 67 to provide a pair of secondary flow passages 96, 98 in the event that the primary inlets/outlets openings 62, 64 of the nares 65, 67, respectively, become either partially or fully occluded, blocked, clogged or otherwise obstructed during use of the nasal cannula 60. The secondary inlets/outlets openings 35 and 37 are smaller than the primary inlet/outlet openings 62, 64 but are large enough to facilitate acquiring breathing information 4, monitoring breathing of a patient via the mouth and/or the nose, sampling the end tidal $CO_2$ content in the exhaled breath of a patient via the mouth and/or the nose to determine the patient's $CO_2$ concentration level in the blood, measuring differential air flow along the tubing connect to the cannula, supplying a treating gas to a patient via the mouth and/or the nose, detecting changes in pressure air flow, or detecting apnea via the mouth and/or the nose, etc.

With respect to the embodiments of FIGS. 8 and 9, it is to be appreciated that it is not necessary to have the first and second mouthpieces 69, 69' precisely centered between the nares 65, 67. It is possible to position the first and second mouthpieces on one side or the other of a central plane P bisecting a center of main body 71 into two halves.

Figure 10:
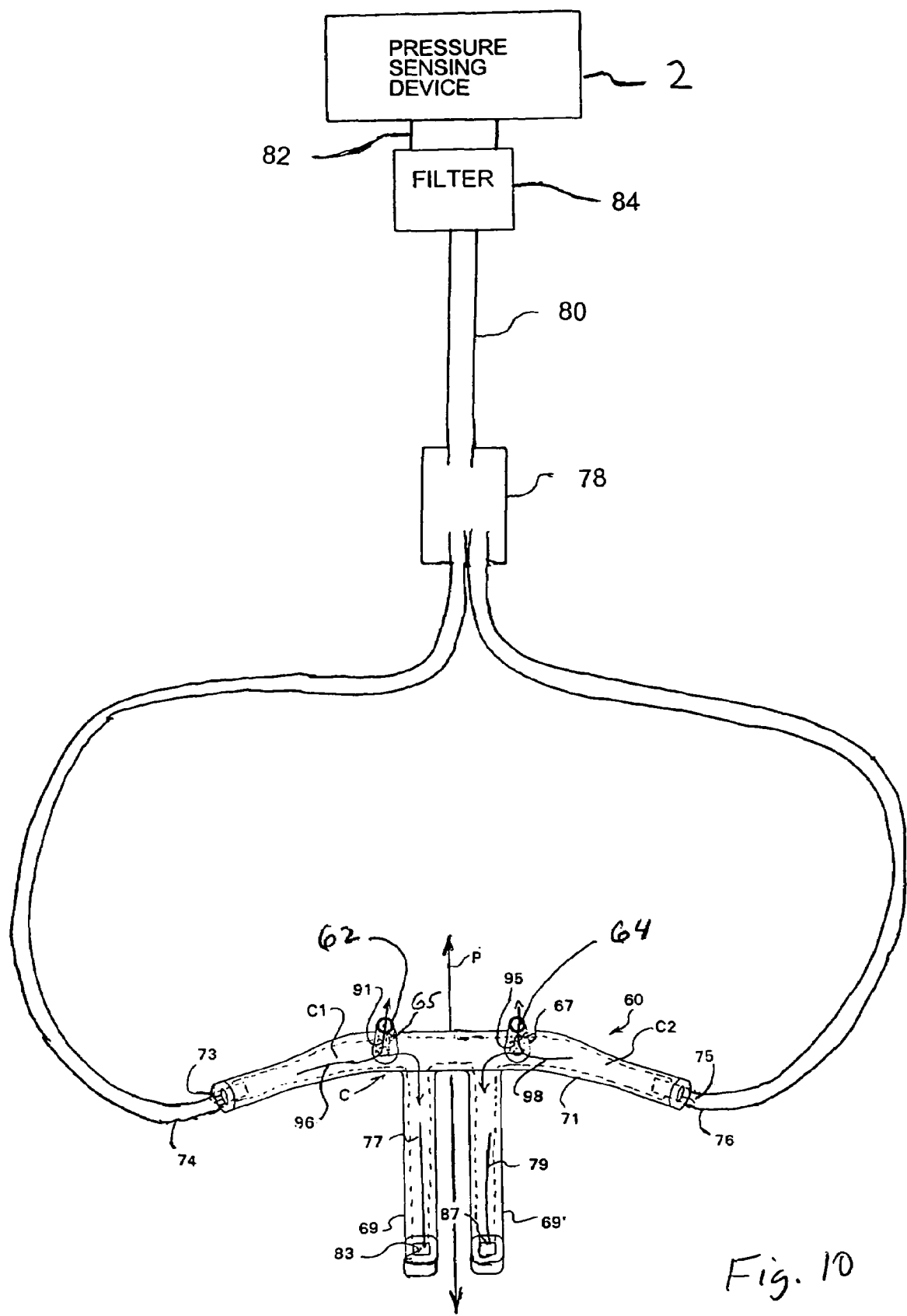
FIG. 10 is a diagrammatic view of an undivided nasal cannula, with a pair of spaced apart mouthpieces but without any secondary openings in the nares, for connection to the pressure sensing device to facilitate acquiring breathing information of a patient.
Figure 11:
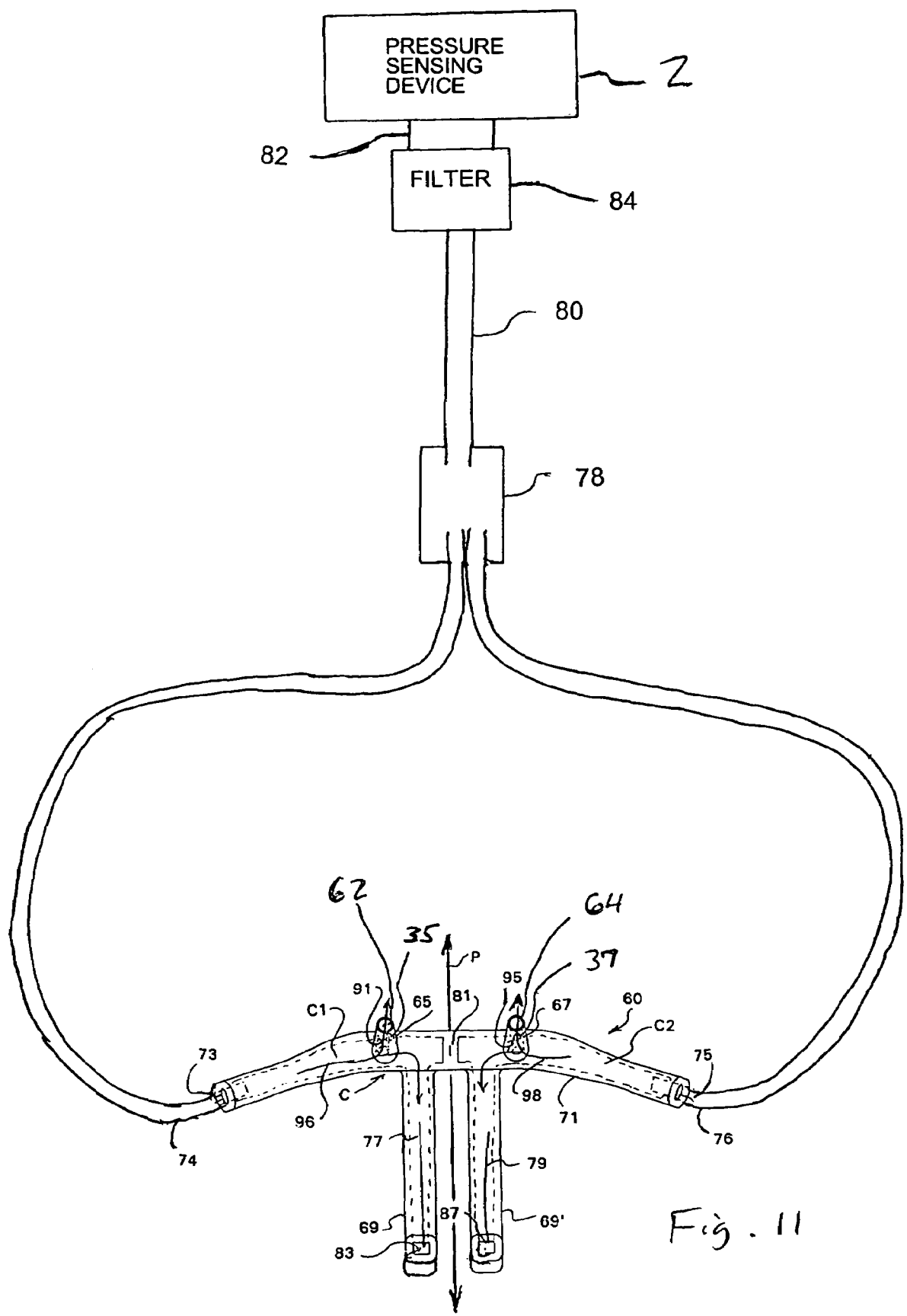
FIG. 11 is a diagrammatic view of an divided nasal cannula, with a pair of spaced apart mouthpieces and with nares having secondary openings therein, for connection to the pressure sensing device to facilitate acquiring breathing information of a patient.

In addition, the first and second mouthpieces could be spaced apart from one another, as shown in FIGS. 10 and 11, so that both of the nares 65, 67 and both of the first and second mouthpieces 69, 69' all communicate with one another via the common central chamber or compartment formed within the main body 71 of the cannula 60. The spacing of the mouthpieces from one another by a distance of from about 0.25 to about 1.25 inches, and more preferably about 0.5 to about 1.0 inches, is useful if the patient being monitored tends to breath, when mouth breathing, out of one side of his or her mouth. By spacing the mouthpieces from one another, mouthpieces of the nasal cannula are better positioned to still detect or monitor breathing of the patient.

In addition, the first and second nares 65, 67 may be each provided with at least one, and preferably a pair of secondary inlets/outlets openings, 35 and 37, adjacent the tip of the nares to provide a pair of secondary flow passages, as shown in FIG. 11 but not in FIG. 10, in the event that the primary inlets/outlets openings 31 of the nares 65, 67 become either partially or fully occluded, blocked, clogged or otherwise obstructed during use of the nasal cannula. The secondary inlets/outlets openings, 35 and 37 are smaller than the primary inlet/outlet opening but are large enough to facilitate acquiring breathing information 4 from the patient, monitoring breathing of a patient via the mouth and/or the nose, sampling the end tidal $CO_2$ content in the exhaled breath of a patient via the mouth and/or the nose to determine the patient's $CO_2$ concentration level in the blood, measuring differential air flow along the tubing connect to the cannula, supplying a treating gas to a patient via the mouth and/or the nose, detecting changes in pressure air flow, or detecting apnea via the mouth and/or the nose, etc.

With reference now to FIG. 12, a detailed description concerning use of strain gauge to provide a test circuit 40 will now be discussed. A further variation of the built-in test circuit 40 would be to replace the battery with a strain gauge 134 and have a strain gauge activation mechanism 136, e.g., an external device for applying strain to the strain gauge 134 in order to generate an electrical current for the test circuit 40. The strain gauge activation mechanism 136 is supported by an exterior surface of the housing 10, preferably on the top surface 14 and at least partially exposed to facilitate actuation thereof. The generated electrical signal could then be passed through the test circuit to the remote free end of each electrical lead 26, 28, 30 and 32, as it is brought into contact with the electrical contact 44 to receive the test output signal 126t, and used to illuminate the light emitting diode 132 and confirm that the electrical lead 26, 28, 30 or 32 is, in fact, operational. The strain gauge 134 would eliminate the need for battery power for the built-in test circuit 40 and allow this circuit to be a passive system.

With reference now to FIG. 13, a description concerning use of a sufficiently thin piezoelectric crystal 138 will now be discussed for use in powering the built-in test circuit 40. According to this variation, the battery of the built-in test circuit 40 is replace with a sufficiently thin piezoelectric crystal 138 and have a piezoelectric crystal activation mechanism 140, e.g., an external device for applying an input stimulus to the piezoelectric crystal 138 and generating an electrical current for the test circuit 40. The piezoelectric crystal activation mechanism 140 is supported by an exterior surface of the housing 10, preferably on the top surface 14 thereof 14, and at least partially exposed to facilitate actuation thereof. The generated electrical signal, from the piezoelectric crystal, could then be passed through the test circuit to the remote free end of each electrical lead 26, 28, 30 and 32, as it is brought into contact with the electrical contact 44 to receive the test output signal 126t, and used to illuminate the light emitting diode 132 and confirm that the electrical lead 26, 28, 30 or 32 is, in fact, operational. The piezoelectric crystal 138 would eliminate the need for battery power for the built-in test circuit 40 and allow this circuit to be a passive system.

With reference now to FIG. 14, a description concerning use of a solar cell 142 will now be discussed for use in powering the built-in test circuit 40. According to this variation, the battery of the built-in test circuit 40 is replace with a solar cell 142 having at least one exposed external for receiving light and converting the received light and generating, via conventional circuitry, an electrical current for the test circuit 40. The generated electrical signal, from the solar cell 142, could then be either stored in a small battery (not shown) or passed through the test circuit to the remote free end of each electrical lead 26, 28, 30 and 32, as it is brought into contact with the electrical contact 44 to receive the test output signal 126t, and used to illuminate the light emitting diode 132 and confirm that the electrical lead 26, 28, 30 or 32 is, in fact, operational. The solar cell 142 would eliminate the need for battery power for the built-in test circuit 40 and allow this circuit to be a passive system.

With reference now to FIG. 15, a description concerning use of a physically activated electrical generator 144, which via motion generates an electrical current, will now be discussed for use in powering the built-in test circuit 40. According to this variation, the battery of the built-in test circuit 40 is replace with physically activated electrical generator 144, such as a magnetic piston 146 captively located within a cylinder 148 which is wrapped with a coil 150 whereby when the end user shakes or moves the pressure sensing device 2 to and fro, such motion causes the magnetic piston 146, to move to and fro along and within the cylinder 148 and induce an electrical current in the wire of the coil 150. This electrical current may then be either stored in a small battery (not shown) or passed through the test circuit to the remote free end of each electrical lead 26, 28, 30 and 32, as it is brought into contact with the electrical contact 44 to receive the test output signal 126t, and used to illuminate the light emitting diode 132 and confirm that the electrical lead 26, 28, 30 or 32 is, in fact, operational. The physically activated electrical generator 144 would eliminate the need for battery power for the built-in test circuit 40 and allow this circuit to be a passive system. It is to be appreciated that other conventional and well known physically activated electrical generators, which generate an electrical current when the end user shakes, moves, operates, actuates, etc., the pressure sensing device 2 would also be suitable for use with the pressure sensing device 2 of the present invention.

If desired, one or both of the mouthpieces 69, 69' of the cannula 60 can be provided with a shape retaining, dead soft material or wire (not shown) to facilitate alignment and retention of the first and/or second mouthpieces 69, 69' in a desired aligned position during use of the cannula 60. The wire permits the mouthpiece 69 or 69' to be bent, configured or molded into a desired shape, configuration or position while still retaining such desired shape, configuration or position following adjustment of the mouthpiece 69 and/or 69'. A copper wire (either insulated or uninsulated), for example, has substantially no structural memory of any previous shape, orientation, configuration or form which would cause the wire to retain, return or spring back to such previous shape, orientation, configuration or form. Copper is a highly malleable metal and generally retains whatever shape is imparted thereto at any particular time without reverting or returning back to any prior or previous shape. Copper is also a preferred dead soft material, over for example iron, steel or other ferromagnetic materials, due to the propensity of the nasal cannula to be used in connection with a patient exposed to certain electromagnetic and magnetic environments and/or diagnosis procedures.

The wire can either be formed integral with the first and/or second mouthpieces 69, 69', can be accommodated within an integral compartment extending along the length of the first and/or second mouthpieces 69 and/or 69', or can be glued or otherwise permanently secured or affixed to an exterior surface of the first and/or second mouthpieces 69 and/or 69', along the entire length thereof, so that the wire 128 does not become separated or dislodged from the cannula 60" during use of the nasal cannula. The wire typically has a diameter of between 0.01 and 0.2 inches or so.

The first and second mouthpieces 69, 69' each have a radius of curvature of between about 0.5 of an inch to about 2.5 inches or so, and more preferably a radius of curvature of between about 0.75 of an inch to about 1.25 inches or so. The radius of curvature of the mouthpieces 69, 69' can vary, depending upon the cannula being manufactured and/or its application, but is generally chosen to facilitate the alignment of an opening formed in the free end of the mouthpiece 69 and/or 69' with the opening of a mouth of the patient. The first and second mouthpieces 69, 69' each define an internal passageway 77, 79 therein which has a transverse cross sectional flow area of between about 0.006 and about 0.007 square inches.

We also in the spirit and scope of the present invention that a pair of output forks which are each associated with a single piezo crystal and a pair of respiratory electric and snore detection circuits can be incorporated in a single exterior housing. It is also anticipated that the piezo electric crystal 8 could be utilized to power three or more respiratory circuits which will all receive the same input signal from a single input port 6.

Since certain changes may be made in the above described improved pressure sensing device, without departing from the spirit and scope of the invention herein involved, it is intended that all of the subject matter of the above description or shown in the accompanying drawings shall be interpreted merely as examples illustrating the inventive concept herein and shall not be construed as limiting the invention.

We claim:

1. A pressure sensing device adapted for coupling to a cannula and receiving respiratory breathing information from a patient to be monitored, the pressure sensing device comprising:
   an exterior housing accommodating an input port, and the input port being coupled to the cannula for receiving the respiratory breathing information from the patient to be monitored;
   the exterior housing accommodating a respiratory snore detection circuit for processing the received respiratory breathing information from the patient and outputting, via a pair of snore electrical leads, a signal indicative of sensed snoring of the patient;
   the exterior housing accommodating a respiratory airflow detection circuit for processing the received respiratory breathing information from the patient and outputting, via a pair of airflow electrical leads, a signal indicative of sensed airflow of the patient; and
   built-in test circuit for testing an integrity of the airflow electrical leads and the snore electrical leads, prior to use of the pressure sensing device, to ensure that the airflow and the snore electrical leads are operational.

2. The pressure sensing device according to claim 1, wherein the input port of the pressure sensing device communicates with a piezo transducer and the piezo transducer is connected to both the respiratory airflow detection circuit and respiratory snore detection circuit for supplying the received respiratory breathing information from the patient thereto.

3. The pressure sensing device according to claim 1, wherein an exterior surface of the housing for the pressure sensing device has an electrical contact for engaging with:
   one of the pair of airflow electrical leads of the respiratory airflow detection circuit and coupling the airflow electrical lead to the test circuit to facilitate testing thereof, and
   one of the pair of snore electrical leads of the respiratory snore detection circuit and coupling the snore electrical lead to the test circuit to facilitate testing thereof.

4. The pressure sensing device according to claim 1, wherein the pressure sensing device is used in combination with a cannula, and the cannula has a pair of nares for insertion into nostrils of the patient to be monitored for acquiring the respiratory breathing information from the patient.

5. The pressure sensing device according to claim 4, wherein the cannula has at least one mouthpiece lumen for acquiring the respiratory breathing information from a mouth of the patient while the patient is mouth breathing.

6. The pressure sensing device according to claim 4, wherein the cannula has a pair of mouthpiece lumens for acquiring the respiratory breathing information from a mouth of the patent while the patient is mouth breathing.

7. The pressure sensing device according to claim 2, wherein the pressure sensing device is used in combination with the cannula, the cannula has a pair of nares for insertion into nostrils of the patient to be monitored for acquiring the respiratory breathing information from the patient, and a filter is provided between a piezo transducer and the cannula for preventing moisture from being transferred from the cannula to the pressure sensing device.

8. The pressure sensing device according to claim 1, wherein the respiratory airflow detection circuit includes an airflow switch which facilitates operation of the respiratory airflow detection circuit in first and second modes, and the second mode of the respiratory airflow detection circuit generates an output amplitude of a processed signal which is less than an output amplitude of a processed signal of the first mode; and the respiratory airflow detection circuit includes a snore switch which facilitates operation of the respiratory snore detection circuit in first and second modes, and the second mode of the respiratory snore detection circuit generates an output amplitude of a processed signal which is less than an output amplitude of a processed signal of the first mode.

9. The pressure sensing device according to claim 8, wherein operation of the respiratory airflow detection circuit in the second mode generates an output amplitude of the processed signal which is about one fourth of the output amplitude of the processed signal of the first mode; and operation of the respiratory snore detection circuit in the second mode generates an output amplitude of the processed signal which is about one fourth of the output amplitude of the processed signal of the first mode.

10. The pressure sensing device according to claim 8, wherein at least one of the airflow switch, for controlling operation of the respiratory airflow detection circuit, and a border surrounding the airflow switch and the airflow electrical leads for the respiratory air pressure circuit are both color coded a first color while at least one of the snore switch, for controlling operation of the respiratory snore detection circuit, and a border surrounding the snore switch and the snore electrical leads for the respiratory snore detection circuit are both color coded a second color which is different from the first color.

11. The pressure sensing device according to claim 1, wherein the input port, for supplying the acquired breathing information to the pressure sensing device, is spaced from a bottom surface of the exterior housing so that when a free end of a cannula is connected to the input port of the pressure sensing device, a connector of the cannula is spaced from a plane defined by the bottom surface of the exterior housing so that the bottom surface of the exterior housing, during use, will always remain flush with and in intimate contact with a support surface for the pressure sensing device to facilitate actuation of the airflow and the snore switches during use of the pressure sensing device.

12. The pressure sensing device according to claim 1, wherein the input port is formed in a top surface of the housing and projects therefrom by a distance of between about 0.1 to about 0.5 inches and extends away from the exterior housing, generally parallel to both the top and bottom surfaces, for a distance of about 0.3 to about 1.5 inches so as to space a connector of the cannula away from the bottom surface of the exterior housing such that the bottom surface of the exterior housing, during use, will always remain flush with and in constant and continuous intimate contact with a support surface for the pressure sensing device.

13. The pressure sensing device according to claim 1, wherein the input port extends away from a side surface of the housing by a distance of between about 0.3 to about 1.5 inches and forms an angle with a bottom surface of the exterior housing of between 140 to about 170 degrees so as to space a connector of the cannula away from the bottom surface of the exterior housing such that the bottom surface of the exterior housing, during use, will always remain flush with and in constant and continuous intimate contact with a support surface for the pressure sensing device.

14. The pressure sensing device according to claim 3, wherein the built-in test circuit is electrically powered by a battery.

15. The pressure sensing device according to claim 3, wherein the built-in test circuit comprises a battery, a resistor and a light emitting diode connected in series with test output signal contact.

16. The pressure sensing device according to claim 3, wherein the built-in test circuit is electrically powered by a solar cell.

17. The pressure sensing device according to claim 3, wherein the test circuit is powered by a piezo electric crystal.

18. The pressure sensing device according to claim 3, wherein the test circuit is powered by a strain gauge.

19. The pressure sensing device according to claim 3, wherein the test circuit is powered by a physically activated electrical generator.

20. A method of using a cannula to receive respiratory breathing information from a patient to be monitored, the method comprising the steps of:
  using a pressure sensing device comprising an exterior housing accommodating an input port,
  coupling the input port to the cannula for receiving the respiratory breathing information from the patient to be monitored;
  accommodating a respiratory snore detection circuit within the exterior housing for processing the received respiratory breathing information from the patient and outputting, via a pair of snare electrical leads, a signal indicative of sensed snoring of the patient;
  accommodating a respiratory airflow detection circuit within the exterior housing for processing the received respiratory breathing information from the patient and outputting, via a pair of airflow electrical leads, a signal indicative of sensed airflow of the patient; and
  testing an integrity of the airflow electrical leads and the snore electrical leads via an internal test circuit, prior to use of the pressure sensing device, to ensure that the airflow and the snore electrical leads are operational.

* * * * *